United States Patent [19]
Maret et al.

[11] Patent Number: 5,665,552
[45] Date of Patent: Sep. 9, 1997

[54] ANTIBODIES TO PLASMODIUM FALCIPARUM

[75] Inventors: S. Melissa Maret, Laytonsville; Hans H. Feindt, Parkton; Gerald DeWayne Hahn, Severn; Keith Uithoven, West Friendship, all of Md.

[73] Assignee: Becton, Dickinson and Company, Franklin Lakes, N.J.

[21] Appl. No.: 408,418

[22] Filed: Mar. 21, 1995

Related U.S. Application Data

[62] Division of Ser. No. 250,309, May 27, 1994, Pat. No. 5,478,741, which is a continuation of Ser. No. 945,287, Sep. 11, 1992, abandoned.

[51] Int. Cl.[6] .......................... G01N 33/53; C07N 15/06
[52] U.S. Cl. .................. 435/7.22; 530/388.6; 530/391.9; 435/34; 436/548
[58] Field of Search ................ 435/7.22, 34; 530/388.6, 530/391.9; 436/548

[56] References Cited

U.S. PATENT DOCUMENTS

| | | | |
|---|---|---|---|
| 5,001,225 | 3/1991 | Taylor et al. | 530/388.6 |
| 5,296,382 | 3/1994 | Wellems et al. | 436/501 |

OTHER PUBLICATIONS

Rock et al. Parasitology 95: 209–227, 1987.

Palfreyman et al. Journal of Immunological Methods, 75 (1984) 383–393.

*Primary Examiner*—Lila Feisee
*Assistant Examiner*—Julie E. Reeves
*Attorney, Agent, or Firm*—Donna R. Fugit

[57] ABSTRACT

Antibodies which recognize and bind to histidine rich protein II of *Plasmodium falciparum*. These antibodies exhibit improved specificity and affinity for the antigen which provides enhanced sensitivity in immunoassays. Peptides useful for generation of the antibodies are also provided.

10 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Cys Gly Ala His His Ala His His Ala Ala Asp Ala His His Ala Ala
1               5                   10                  15
Asp Ala
```

ANTIBODIES TO PLASMODIUM FALCIPARUM

This is a division of application Ser. No. 08/250,309, filed May 27, 1994, which has issued as U.S. Pat. No. 5,478,741 on 26 Dec. 1995, which is a continuation of application Ser. No. 07/945,287, filed on Sep. 11, 1992 (abandoned).

FIELD OF THE INVENTION

The present invention relates to antibodies which recognize and bind to HRP-II, a histidine-rich protein of *Plasmodium falciparum*, assays employing these antibodies, and peptides for generating the antibodies.

BACKGROUND OF THE INVENTION

*Plasmodium falciparum* is the most pathogenic species of human malaria. The asexual parasites of this species in red blood cells produce several proteins characterized by an unusually high content of the amino acid histidine. One of these proteins is designated Histidine Rich Protein II (HRP-II). HRP-II is synthesized throughout the asexual stage of the parasite and is released from infected cells into the blood stream.

The HRP-II gene has been isolated and sequenced. The predicted amino acid sequence includes 34% histidine, 37% alanine and 10% aspartic acid (Wellems and Howard. 1986. PNAS 83, 6065–6069). The HRP-II protein is also unusual in that it contains many tandem repeats of the amino acid sequences Ala-His-His and a related sequence comprising about 80% of the sequence of the protein (Wellems and Howard, 1986 supra). The functions of HRP-II and the other histidine-rich proteins are not yet known, but HRP-II is of particular interest for early detection of malarial infection because it is transported out of infected cells into the extracellular medium where it can be detected in the blood of infected patients. Highly sensitive immunoassays for detection of HRP-II are therefore desirable as a means for detecting malaria infection at an early stage of the disease.

Antibodies specific for HRP-II are known in the art. Monoclonal antibody MAb-87 and its subclones, raised to the intact HRP-II protein, have been described by Howard, et al. (1986) J. Cell Biol. 103, 1269–1277; Rock, et al. (1987) Parasitology 95, 209–227 and Panton, et al. (1989) Molec. Biochem. Parasitology 35, 149–160. MAb-87 and its subclones are also disclosed in WO 89/01785 to Taylor. However, Mab-87 and its related monoclonals are not suitable for diagnosis of malaria, as they are capable of detecting a minimum of only 0.05% parasitemia in an enzyme linked immunosorbent assay (ELISA). Suppl. to Amer. J. Trop. Med. Hyg. 1991. 45(3): 248–249. Polyclonal antibodies to a fragment of the HRP-II protein containing Ala-His-His and Ala-Ala-Asp repeats have been reported by Knapp, et al. (1988. Behring Inst. Mitt. 82, 349–359). Wellems, et al. (1987. Cell 49, 633–642) have produced polyclonal antisera to a synthetic peptide having a similar amino acid sequence and these antibodies bind to the HRP-II protein. Wellems and Howard disclose these same polyclonal antisera and synthetic peptide in U.S. Pat. No. 5,130,416. The foregoing authors and inventors also describe the use of the various anti-HRP-II antibodies to detect HRP-II antigen in immunoassays such as Western blots and ELISA's.

SUMMARY OF THE INVENTION

The present invention provides antibodies which recognize and bind to HRP-II with increased specificity and affinity, thereby providing increased sensitivity in immunoassays as compared to prior art anti-HRP-II antibodies. Monoclonal antibodies as well as polyclonal antisera were generated by immunization with a unique synthetic peptide comprising the amino acid sequence (SEQ ID NO:1):

Cys—Gly—Ala—His—His—Ala—His—His—Ala—Ala—Asp—

Ala—His—His—Ala—Ala—Asp—Ala.

The N-terminal cysteine facilitates coupling of the peptide to maleimide-derivatized carrier proteins through its —SH group. It is believed that the cysteine along with the glycine in the second position serve as a spacer linkage between the HRP-II-like sequence and the carrier protein which permits the peptide to assume a more authentic conformation for the production of antibodies. J. B. Rothbard et al. J. Exp. Med. 1984, 160: 208–221.

DETAILED DESCRIPTION OF THE INVENTION

The antibodies of the invention exhibit significantly improved specificity and affinity for HRP-II antigen in immunoassays as compared to the antibodies described in the prior art. They therefore increase the sensitivity of immunoassays and represent an important advance in the ability of clinicians to detect the disease at an early stage. The antibodies of the invention are capable of detecting as little as 0.0008% parasitemia in plasma and 0.0002% parasitemia in whole blood, whereas an ELISA employing prior art antibodies could reliably detect only parasitemias of 0.05% or greater (Schaeffler et al. 1991. Program & Abstracts of the 40th Annual Meeting of American Society of Tropical Medicine and Hygiene. Abstract #384. Amer. J. Trop. Med. Hyg. Suppl. 45(3): 248–249). The percent parasitemia is determined by evaluating the number of infected red blood cells vs. uninfected red blood cells in a stained blood film and is a reflection of the degree of infection. The improved antibodies of the invention are intended to encompass both polyclonal and monoclonal antibodies having the disclosed properties.

Taylor's prior art antibodies, as described in JCB (1986) 103, 1269, were produced in mice immunized with emulsified, purified red blood cells infected with whole parasites. In contrast, the improved antibodies of the invention were generated by immunizing mice with a synthetic peptide which is a modification of the peptide described by Wellems and Howard in U.S. Pat. No. 5,130,416.

The immunogenic peptide has the amino acid sequence of SEQ ID NO:1:

Cys—Gly—Ala—His—His—Ala—His—His—Ala—Ala—Asp—

Ala—His—His—Ala—Ala—Asp—Ala.

wherein Cys represents the N-terminus of the peptide and Ala represents the C-terminus. Residues 3–17 are a histidine-rich repeat sequence similar to segments of native HRP-II. The peptide may be synthesized using any of the synthetic methods known in the art, for example the solid-phase method of Merrifield (1969. Advan. Enzymol. 32:221) or the modified solid-phase methods of Sheppard and Atherton (WO 86/03494) which are now automated. Chemical synthesis of the peptide is preferred.

An alternative method for producing the immunogenic peptide is by expression of a recombinant oligonucleotide coding for the 18-mer. Methods for synthesizing an appropriate nucleic acid sequence, cloning it and expressing it in a transformed host cell are well known and within the ordinary skill in the art.

The cysteine residue at the N-terminus of the peptide facilitates coupling of the peptide to an immunogenic carrier through the —SH group of cysteine. Coupling of the peptide to an immunogenic carrier is preferred for immunization, as coupling allows the small antigenic determinant peptide (a hapten) to elicit an antibody response. Commonly used immunogenic carriers useful for coupling to haptens such as the peptide of the invention are listed in *Immunology, An Illustrated Outline* by David Male, Gower Medical Publishing, 1986, pg. 31. Keyhole limpet haemocyanin (KLH) is the preferred immunogenic carrier for coupling to the peptide to generate the antibody response.

The N-terminal Cys-Gly serves as a spacer linkage between the carrier and the peptide. While not wishing to be limited to any particular method by which the invention operates, Applicants believe that by providing such a spacer linkage, the negative effects of the carrier on the conformation of the peptide may be reduced, thus allowing the peptide to assume a conformation more characteristic of a naturally occurring epitope of the HRP-II protein. This more authentic conformation may contribute to the ability of the peptide to elicit the surprisingly high sensitivity antibodies of the invention.

Methods for coupling carriers to haptens through sulfhydryl groups are known in the art and any of these are suitable for coupling the selected carrier to the immunogenic peptide. For example, see the coupling protocols described in *Current Protocols in Immunology*, J. E. Coligan et al., eds., Greene Publishing Assoc. and Wiley Interscience, 1992, Chapter 9. Preferred reagents for coupling the sulfhydryl of cysteine to an amino group of a carrier protein are sulfosuccinimidyl 4-(N-maleimidomethyl) cyclohexane-1-carboxylate (sulfo SMCC) or SMCC and m-maleimidobenzoyl-N-hydroxysuccinimide (MBS) or sulfo-MBS because they are specific for Cys-SH with essentially no secondary coupling reactions at other amino acid residues. The most preferred coupling reagent is sulfo SMCC, which may be used to conjugate the hapten to the peptide according to known methods such as S. Hashida et al. (1984) J. Applied Biochemistry 56: 56–63. However, other coupling reagents such as glutaraldehyde may also be used with some secondary reaction at the histidine residues.

The Ala residue at the C-terminus of the peptide serves to reduce the negative charge density at the C-terminus and represents the next amino acid which would be present in the native HRP-II protein.

Suitable methods for immunizing animals with synthetic peptides are also well known in the art. See *Current Protocols in Immunology*, supra. In general, an immunogenic amount of peptide/carrier conjugate is dissolved or suspended in a physiological buffer, e.g., phosphate buffered saline (PBS), usually mixed with an adjuvant such as complete Freunds adjuvant. Animals are initially immunized with this mixture and thereafter boosted with additional doses of peptide/carrier conjugate. The immunization with peptide/carrier conjugate is then repeated with an adjuvant such as incomplete Freunds adjuvant. At about 7 and 12 weeks after the initial immunization the serum is generally tested using methods known in the art to determine the titer of antipeptide antibodies (e.g., reactivity with the immunogen in an ELISA). Modifications and adjustments to this basic immunization protocol to obtain optimal antipeptide antibody titers for any particular peptide/carrier conjugate are within the ordinary skill in the art. If purified polyclonal antibody is desired, it may be isolated from the immune serum using well-established methods, such as separation on a peptide affinity column.

The spleen cells of an animal immunized with the immunogenic peptide may also be fused with murine myeloma cells for production of monoclonal antibodies using the method of Kohler and Milstein (1975. Nature 256, 495–497) or other modifications of this method known in the art (Oi and Herzenberg. 1980. *Selected Methods in Cellular Immunology*, Mishell and Shiigi, eds., pp. 351–372, W. H. Freeman, New York; Goding. 1986. *Monoclonal Antibodies: Principles and Practice*. Academic Press, San Diego). The fused cells are cloned and screened for production of the desired anti-peptide monoclonal antibody using immunological assays such as ELISAs. If desired, purification of monoclonal antibody from hybridoma culture supernatants or ascites fluid may be accomplished using methods known in the art, e.g., Protein G or peptide affinity column chromatography.

The isolated polyclonal and monoclonal antibodies produced in response to immunization with the peptide may be used in immunoassay protocols of several types. The antibodies may be used intact or fragments may be generated which are also capable of binding to the peptide and HRP-II protein (Fab or F(ab')$_2$). Intact antibodies as well as antigen binding fragments thereof are intended to be encompassed by the present invention. While immunoassays can be performed using only polyclonal antibody reagents, in most cases monoclonal antibody or a combination of polyclonal and monoclonal antibodies are preferred. In general, antibodies or antigens in immunoassays are labeled by conjugation to a detectable label to facilitate detection of antigen/antibody binding by inclusion of the label in the binding complexes formed. As used herein, the term "label", "detectable label" and related terms are intended to encompass both the detectable label alone and, as described below, detectable labels associated with particles. Suitable labels and methods for conjugating them to proteins such as antibodies are well known. Directly detectable labels, which do not require additional reagents or reaction to be detected, include radioisotopes, fluorescent dyes and visible absorbing dyes. Enzymes capable of reacting to produce colored products are suitable indirectly detectable labels commonly used for conjugation to antibodies in specific binding assays. All of the foregoing labels are suitable for conjugation to the polyclonal and monoclonal antibodies of the invention.

Particulate detectable labels are preferred for conjugation to the antibodies. Such particles include particles of polymers (e.g., latex or polystyrene), sacs, liposomes, metallic sols (e.g., colloidal silver or colloidal gold), other colloidal particles or polymeric dyes. To form the particulate label, the particles are derivatized to include the selected detectable label, usually by formation of a chemical bond using methods known in the art for this purpose. Polisher particles, such as latex particles, may also have the dye incorporated into the polymer. In the case of sacs and liposomes, the label may also be entrapped in the vesicle. The particle and its associated label may then be chemically conjugated to the antibody for use in specific binding assays. Alternatively, polymer particles, polymeric dyes and metal particles may be coated with the antibody as described in U.S. Pat. No. 5,096,837. The preferred detectable labels for association with the present antibodies are liposomes encapsulating an entrapped visible dye or other colored particles, with the antibody coupled to the surface of the liposome or particle. Such liposome labels are described in U.S. Pat. No. 4,695,554.

The protocols for immunoassays using the antibodies are well known in the art. For example, polyclonal or monoclonal antibodies according to the invention or antigen binding fragments thereof may be employed in sandwich assays for detecting HRP-II protein or in the known modifications and variations of sandwich assay protocols. Alternatively, the antibodies and antigen binding fragments thereof may be employed in various competitive assay formats as are known in the art. The basics of these assay protocols are reviewed in *Current Protocols in Immunology*, supra. When used as a diagnostic for malaria infection, it is preferred that the sample tested for the presence of HRP-II protein be either lysed or unlysed blood. However, other samples may be assayed as well, for example, supernatants of infected cell cultures, extracts of *P. falciparum* parasites, serum, plasma, urine and cerebrospinal fluid.

Devices for performing specific binding assays, especially immunoassays, are known and can be readily adapted for use with the present monoclonal and polyclonal antibodies for detection of HRP-II. Solid-phase assays, in general, are easier to perform than heterogeneous assay methods such as precipitation assays because separation of reagents is faster and simpler. Solid-phase assay devices include microtiter plates, flow-through assay devices, dipsticks and immunocapillary or immunochromatographic immunoassay devices as described in U.S. Pat. No. 4,743,560; U.S. Pat. No. 4,703,017; U.S. Pat. No. 4,666,866; U.S. Pat. No. 4,366,241; U.S. Pat. No. 4,818,677; U.S. Pat. No. 4,632,901; U.S. Pat. No. 4,727,019; U.S. Pat. No. 4,920,046; U.S. Pat. No. 4,855,240; U.S. Pat. No. 5,030,558; U.S. Pat. No. 4,168,146. Most preferred are immunocapillary assay devices which can be used as a dipstick, employing the inventive monoclonal or polyclonal antibodies.

The preferred immunocapillary dipstick assay device is designed for conducting a sandwich immunoassay for HRP-II antigen. It comprises a piece of microporous absorbent material such as nitrocellulose laminated to a plastic backing. In contact with the microporous material is a strip of a second absorbent material such as glass fiber, also laminated to the plastic backing. Nitrocellulose is preferred for the first material because it allows immobilization of protein simply by applying the protein solution to the nitrocellulose and allowing it to be absorbed. The second absorbent is in fluid communication with the microporous material and assists in pulling the assay fluids through the microporous absorbent. The second absorbent also absorbs the fluids which pass through the microporous material.

A monoclonal antibody according to the invention is immobilized on the microporous absorbent in a position where it will not be directly immersed in the sample being tested. To perform the assay the portion of the microporous absorbent below the monoclonal antibody is contacted with the sample such that the sample fluid is drawn up into it by capillarity (wicking), thus bringing the sample into contact with the antibody and allowing binding between the antibody and any HRP-II antigen which may be present in the sample. Thereafter, a solution containing a visible dye-labeled polyclonal antibody according to the invention is wicked up into the microporous absorbent into contact with the monoclonal antibody/bound antigen complex such that the polyclonal antibody binds to the complexes through interaction with HRP-II. Optionally, a wash solution containing a mild detergent which will not disrupt the liposomes (e.g., ZWITTERGENT) may be wicked into the microporous absorbent after binding of the polyclonal antibody. The detectable dye label is then visualized in the area of immobilized monoclonal antibody.

In a preferred alternative embodiment of the dipstick assay device, a positive control area is included on the microporous absorbent in the vicinity of but distinct from the immobilized monoclonal antibody. The positive control may be HRP-II antigen, the immunogenic peptide or a derivative or analog thereof which also binds the antibodies of the invention. The preferred positive control is HRP-II antigen immobilized on nitrocellulose in an area contacted by the migrating sample fluid after it contacts the area of immobilized monoclonal antibody.

The selected device and reagents for performing the immunoassay may be packaged in the form of a kit for convenience. For example, such a kit may include an appropriate assay device, antibody reagents, reagents for development of the assay such as buffers and, if needed, reagents for detection of the chosen label.

The inventive antibodies may also be useful for reducing the risk of *P. falciparum* infection or treating such infection once established. Treatment may be accomplished by administering to an animal suffering from malaria infection, preferably a human, a therapeutically effective amount of a pharmaceutical composition comprising a monoclonal or polyclonal antibody according to the invention. Similar pharmaceutically acceptable compositions may be administered to an animal in a dose sufficient to increase immunity to subsequent *P. falciparum* infection. Alternatively, anti-idiotypic antibodies raised against the inventive monoclonal or polyclonal antibodies may also be administered in a pharmaceutical composition as a vaccine against malaria infection.

The following experimental Examples are intended to illustrate certain features and embodiments of the invention but are not to be considered as limiting the scope of the invention as defined by the appended claims.

EXAMPLE 1

An 18-mer peptide having the amino acid sequence of SEQ ID NO:1 was prepared using Fmoc-mediated synthetic chemistry with BOP and HOBT essentially as described by D. Hudson (1988. J. Org. Chem. 53: 617–624). A Milligen/Bio-Search EXCELL solid phase peptide synthesizer was used as recommended by the manufacturer to perform the synthesis. The completed peptide was deprotected and cleaved from the resin using Reagent R as recommended by Milligen/BioSearch in their instructions. Crude peptide was isolated by centrifuging the precipitate formed upon addition of seven volumes of cold diethyl ether to combined Reagent R and trifluoroacetic acid (TFA) washes of the resin. The precipitate was washed with cold diethyl ether and subsequently dried in vacuo. Crude peptide was further purified by chromatography on a $C_{18}$-reverse phase matrix eluted with a gradient of 0.1% TFA in water (Buffer A) and 0.1% TFA in acetonitrile (Buffer B). The 18-mer peptide eluted at 33–34% Buffer B and was subsequently collected by lyophilizing pooled fractions containing the peptide. Conjugation of the purified peptide to sulfo-SMCC derivatized keyhole limpet hemocyanin (KLH) was done as described by Rothbard, et al. (1984. J. Exp. Med. 160: 208–221) with minor modifications. Peptide conjugate was isolated from unconjugated peptide by chromatography on Sephadex G-75. The purified 18-mer peptide:KLH conjugate was subsequently used as an immunogen for eliciting antibodies to HRP-II.

Male BalbC/AnCrl mice (18–20 g) were used for immunization. A 2 mg/ml stock solution of the immunogenic peptide was prepared by reconstituting 8 mg of lyophilized peptide in 4.0 ml of prewarmed PBS with vortex mixing until the powder dissolved. The stock solution was diluted 1:1 with PBS and the 1 mg/ml solution was used for immunization. The first two injections were given in the footpad and subcutaneously (100 µl at each site of 1 mg/ml peptide:KLH with 100 µl Complete Freunds Adjuvant, Difco). This was followed by four intraperitoneal injections of 100 µl of peptide:KLH at approximately two day intervals. Anti-18-mer titers were evaluated, and three of the four mice immunized responded well to the peptide. Two intraperitoneal injections of 100 µl of peptide:KLH were then given at approximately weekly intervals. After these injections, all four mice had some immune response to the peptide. Approximately three months later the mice were boosted with four intraperitoneal injections of peptide:KLH. Based on reactivity with the 18-mer peptide in an ELISA, one was selected for fusion of the splenocytes with P3 myeloma cells according to a standard protocol such as that described in "Current Protocols in Immunology," J. E. Coligan et al., eds., 1991, John Wiley & Sons, Chapter 2.

For screening immunized mice or hybridomas, ELISA plates were coated overnight at 4° C. with 20 µg/ml of unconjugated 18-mer peptide, peptide conjugated to KLH (the immunogen) or peptide conjugated to BSA. Bleeds from immunized mice prior to splenocyte fusion or hybridoma culture supernatants were diluted 1:10 in PBS-Tween buffer, followed by serial two-fold dilutions thereafter. The dilutions were incubated in the prepared ELISA plates for 1 hr at room temperature. Horseradish peroxidase conjugated goat anti-mouse immunoglobulin or rabbit anti-mouse IgG antibody was diluted in PBS-Tween and incubated with the ELISA plates for 1 hr. O-phenylenediamine dihydrochloride enzyme substrate was diluted in titrate-phosphate buffer and incubated with the ELISA plates for 10 min. at room temperature. The absorbance of the medium was read at $A_{490}$.

Hybridomas resulting from the fusion were cloned and expanded based on reactivity with peptide:KLH in the ELISA. Clone MAL 18-27 was found to be the only clone reactive with both the unconjugated peptide and the conjugated peptide, indicating that the antibody produced was specific for the peptide rather than the KLH. MAL 18-27 was also shown to be 18-mer specific, as it was the only clone tested which did not also react with a 10-mer and/or a 21-mer in the ELISA. An isotyping assay of clone MAL 18-27 showed the antibody produced to be an IgG1k isotype.

As it demonstrated the desired specificities, clone MAL 18-27 was further subcloned. Two of these subclones, MAL 18-27.2.3.1 and MAL 18-27.2.3.1.2, have been deposited with the American Type Culture Collection, Rockville, Md. on Sep. 3, 1992 under Accession Numbers HB11111 and HB11112, respectively.

Monoclonal antibody MAL 18-27.2.3.1, the parent clone of MAL 18-27.2.3.1.2, was tested in a solid phase dipstick immunoassay. The immunocapillary dipstick device comprised a strip of nitrocellulose (Schleicher & Schuell, Keene, N.H.) 7 mm wide and 25 mm long laminated to a plastic backing strip. A strip of glass fiber (Gelman, Ann Arbor, Mich.) 7 mm wide and 5 cm long was also laminated to the plastic backing such that the glass fiber was in contact with and slightly overlapped the upper edge of the nitrocellulose. One µg of monoclonal antibody MAL 18-27.2.3.1 was spotted on the nitrocellulose in the form of a line at approximately the midportion of the nitrocellulose strip. Approximately 6 mm above the line, 0.17 µg of isolated HRP-II antigen was spotted on the nitrocellulose in a dashed line. The HRP-II antigen served as a positive control in the immunoassay.

The bottom edge of the nitrocellulose was placed in a shallow well containing a 50 µl sample of lysed whole blood, serum or plasma such that the sample fluid was wicked up into the nitrocellulose and brought into contact with the immobilized antibody, allowing HRP-II antigen present in the sample to bind. A drop of a tracer reagent comprising rabbit polyclonal antibody raised against the immunogenic peptide incorporated into liposomes with entrapped sulforhodamine B was placed in the well and wicked up into the nitrocellulose. The tracer reagent also contacted and became bound to sample antigen complexed with the immobilized monoclonal antibody. A wash reagent comprising 0.125% ZWITTERGENT 3-10 (Calbiochem, LaJolla, Calif.) was then wicked into the nitrocellulose.

In positive samples, the dye was visible in a line at the midpoint of the nitrocellulose, indicating a positive assay. The dashed line 6 mm above the midpoint also bound the labeled polyclonal antibody, indicating that the device and reagents were performing correctly.

One patient with 40 parasites/µl of plasma (corresponding to 0.0008% parasitemia) gave a clear 1+ positive response in the dipstick assay. Two patients with 2 parasites/100 white blood cells in whole blood samples (corresponding to 0.003% parasitemia) gave a very strong 3–4+ positive response in the dipstick assay.

EXAMPLE 2

The titer of monoclonal antibody MAL 18-27.2.3.1 to the peptide antigen was compared to Mab 87-2G12 (WO 89/01785) as a measure of antibody specificity. Each well of a 96-well microtiter plate was coated with 50 µl of a 20 µg/ml solution of peptide antigen in 0.1M carbonate buffer, pH 9.6 and incubated at 37° C., covered, overnight. The wells were washed five times with 200 µl of PBS-0.05% Tween 20 buffer. Protein G purified monoclonal antibodies were serially diluted into the wells (50 µl/well), starting at a protein concentration of 20 µg/ml. The antibodies were allowed to bind to the immobilized antigen at 37°, covered for 1 hr. and the wells were washed five times with 200 µl of PBS-0.05% Tween 20 buffer.

Horse radish peroxidase (HRP) labeled goat anti-mouse Ig (Organon Teknika, Durham, N.C.) was added at a 1:8,000 dilution in PBS-0.05% Tween 20 buffer, 50 µl/well, and incubated 1 hr. at 37° C., covered. The wells were washed as above and 50 µl of O-phenylenediamine dihydrochloride (the enzyme substrate) were added for 10 min. at room temperature. The enzyme reaction was quenched by adding 50 µl/well of 4.5M $H_2SO_4$.

The titer was calculated as the antibody concentration which gave an $OD_{490}$ of 1.00. The Mab 87-2G12 resulted in an OD reading of about 0.42 at 20 µg/ml, indicating that a titer of greater than 20 µg/ml would be necessary for an OD reading of 1.00. The inventive monoclonal antibody MAL 18-27.2.3.1, in contrast, had a titer of 1.79 µg/ml and therefore exhibits a significantly higher specific activity for the peptide antigen. That is, to determine a fixed amount of peptide with an intensity of 1.00 OD units, only 1.79 µg/ml of MAL 18-27.2.3.1 is required as compared to more than 20 µg/ml of Mab 2G12.

In a second comparison, MAL 18-27.2.3.1 was tested against Mab 87-1E1 (WO 89/01785) for antigen titer. The wells were coated with 50 µl/well of Protein G purified monoclonal antibody (10 µg/ml in 0.1M carbonate buffer) at 4° C. overnight. The plates were washed five times on a Biotek EL403 automated 96 well washer. The peptide antigen was serially diluted into the coated wells of the microtiter plates (50µl/well, starting at 10 µg/ml) and incubated at 37° C. for 1 hr., covered, with shaking. The plates were again washed five times on the Biotek washer.

10 μg/ml solutions of the detector antibodies were prepared in PBS-0.05% Tween 20 buffer and 50 μl/well was added to the antigen captured plates. The plates were incubated 1 hr. at 37° covered with shaking. To ensure that both ELISA's were optimized to their maximum detection ability, a monoclonal detector antibody was used for assay of Mab 87-1E1 but the rabbit polyclonal detector antibody described in Example 1 was used to assay MAL 18-27.2.3.1.

Using Mab 87-1E1 as the capture antibody, about 144 μg/ml of peptide antigen was required to give an average OD reading of 1.0. Using MAL 18-27.2.3.1 as the capture antibody, only 0.8–1.2 μg/ml of peptide antigen was required for an average OD reading of 1.0. These results demonstrate a significantly higher sensitivity in the assay using the inventive antibody.

EXAMPLE 3

Monoclonal antibody MAL 18-27.2.3.1.2 was clinically tested in comparison with a commercially available diagnostic test (QBC, Becton Dickinson Advanced Diagnostics, Baltimore, Md.) as a diagnostic for *P. falciparum* infection using the dipstick assay format previously described. QBC results were confirmed by microscopic analysis of thin films. All tests were performed on anticoagulated venous blood samples aged 2–24 hrs. and kept under refrigeration. Tests were also performed after four days on three samples The twelve samples which tested positive by QBC and thin films also tested positive in the dipstick assay. One of these samples was from a patient exhibiting only gametocytes. The dipstick assay was positive for parasitemias below 0.1%, including one parasitemia which showed only 3 parasites on the thin film.

One patient followed for five days showed an initial parasitemia of 4% which progressed to rare trophoblasts, then rare gametocytes on the thin films. However, at each stage the dipstick assay was clearly positive.

Twenty-one patient samples which tested negative by QBC and thin films were tested with the dipstick assay. Three of these patients, with proven *P. falciparum* malaria, had been treated with intravenous quinine therapy. After three days their QBC and films remained negative, but the patients tested positive with the dipstick assay for as long as six days.

These results demonstrate that antibodies raised to the 18-mer peptide have increased specificity and sensitivity in clinical tests as compared to anti-*P. falciparum* antibodies currently used in diagnostics.

What is claimed is:

1. A method for detecting HRP-II of *Plasmodium falciparum* comprising the steps of:
    a) contacting a sample with a monoclonal antibody produced by a hybridoma having ATCC Accession No. HB11111 or Accession No. HB11112;
    b) allowing the antibody to bind to the HRP-II to form an antibody/HRP-II complex, and;
    c) detecting the HRP-II by means of a detectable label included in the complex.

2. The method of claim 1 wherein the HRP-II is detected on a solid phase.

3. The method of claim 2 wherein the HRP-II is detected on an immunocapillary solid phase.

4. The method of claim 1 or 3 wherein the HRP-II is detected by means of a second antibody which binds to the HRP-II, the second antibody being conjugated to the detectable label.

5. The method of claim 4 wherein the HRP-II is detected by means of a liposome coupled to the second antibody, the liposome encapsulating a visible dye.

6. The method of claim 1 wherein the HRP-II and HRP-II conjugated to a label compete for binding to the antibody.

7. An immunoassay device comprising a microporous absorbent material in fluid communication with a second absorbent material, the microporous absorbent material having immobilized thereon a monoclonal antibody produced by a hybridoma having ATCC Accession No. HB11111 or Accession No. HB11112.

8. The immunoassay device of claim 7 wherein the microporous absorbent material is nitrocellulose and the second absorbent material is glass fiber.

9. The immunoassay device of claim 8 which includes a positive control area comprising HRP-II antigen.

10. A kit of materials for performing an enzyme linked immunoassay for HRP-II of *Plasmodium falciparum* comprising:
    a) an assay device according to claim 7, and;
    b) a reagent comprising liposomes coupled to a polyclonal antibody to HRP-II, the liposomes encapsulating a visible dye.

* * * * *